US006203776B1

(12) United States Patent
Bristow et al.

(10) Patent No.: US 6,203,776 B1
(45) Date of Patent: Mar. 20, 2001

(54) METHOD FOR IDENTIFYING ADRENERGIC RECEPTOR ANTAGONISTS HAVING GOOD TOLERABILITY

(75) Inventors: Michael R. Bristow, Greenwood Village; J. David Port, Denver, both of CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/047,755

(22) Filed: Mar. 25, 1998

Related U.S. Application Data

(60) Provisional application No. 60/043,906, filed on Apr. 3, 1997.

(51) Int. Cl.[7] .................................................. A61K 49/00
(52) U.S. Cl. .......................... 424/9.2; 424/9.1; 424/1.11; 424/198.1; 424/520
(58) Field of Search .......................... 552/502; 564/365; 424/1.11, 1.65, 9.1, 9.2, 198.1, 520; 514/805; 530/389.2, 399; 436/86; 536/23.51

(56) References Cited

U.S. PATENT DOCUMENTS 4,011,258 * 3/1977 Wetterlin et al. ..................... 260/479
5,403,590 * 4/1995 Forse ..................................... 424/422

OTHER PUBLICATIONS

Bond et al., 1995, *Nature*, 374:272–276.
Bradford, 1976, *Analytical Biochemistry*, 72:248–254.
Bristow et al., 1988, *Journal of Pharmacology and Experimental Therapeutics*, 247(3): 1039–1045.
Bristow et al., 1992, *J Cardovasc Pharmacol.*, 19(Suppl. 1):S68–S80.
Bristow et al., 1992, *J. Clin. Invest.*, 70:S105–S113.
Chidiac et al., 1993, *Mol Pharmacol.*, 45:490–499.
Kenakin, 1996, *Pharmacol. Reviews*, 48(30):413–463.
Landzberg et al., 1991, *Circulation*, 84(4):1608–1614.
Lowes et al., "Clinical Relevance of Inverse Agonism and Guanine Nucleotide Modulatable Binding Properties of β Adrenergic Receptor Blocking Agents", American Heart Assoc. Annual Mtg., I–543 (abstract 2925) (Nov. 1994).
Monopoli et al., 1989, *J. Cardiovasc Pharmacol.*, 14:114–120.
Samama et al., 1993, *J. Biological Chemistry*, 268(7):4625–4636.
Samama et al., 1994, *Molecular Pharmacol.*, 45:390–394.
Sponer et al., 1987, *J Cardiovasc Pharmacol.*, 9:317–327.
Tate et al., 1991, *Eur. J. Biochem.*, 196:357–361.
Yoshikawa et al., 1996, *European Heart Journal*, 17(Suppl. B):8–16.
Allard, 1995, *Journal of Pharmacology and Experimental Therapeutics*, 274(1):577–583.
Dohlman et al., 1988, *Biochemistry*, 27:1813–1817.
Emorine et al., 1987, *Proc. Natl. Acad. Sci. USA*, 84:6995–6999.
Heart Disease, E. Braunwald, ed., pp. 486–488, 610–613 and 853 (5th ed. 1997).
Milano et al., 1994, *Science*, 264:582–586.
Dox et al, p. 460, The Harper Collins Illustrated Medical Dictionary, 1993.*

* cited by examiner

*Primary Examiner*—Dameron Jones
(74) *Attorney, Agent, or Firm*—Fulbright & Jaworski

(57) ABSTRACT

Disclosed are methods to identify adrenergic receptor antagonists having good tolerability. These methods include measuring the inverse agonist activity and/or the intrinsic sympathomimetic activity of an adrenergic receptor antagonist. Also disclosed are a method to treat heart failure and compounds useful therefor.

28 Claims, 1 Drawing Sheet

METHOD FOR IDENTIFYING ADRENERGIC RECEPTOR ANTAGONISTS HAVING GOOD TOLERABILITY

This application claims benefit of provisional application Ser. No. 60/043,906, filed Apr. 3, 1997.

This invention was made with support from the government under National Institutes Of Health grants HL 48013 and HL 51239. The government has rights in the invention.

FIELD OF THE INVENTION

The present invention relates to a method to identify adrenergic receptor antagonists having good tolerability for the treatment of heart failure. More particularly, the present invention relates to the identification of adrenergic receptor antagonists having good tolerability by measuring the inverse agonist activity and the intrinsic sympathomimetic activity of such adrenergic receptor antagonists.

BACKGROUND OF THE INVENTION

A variety of human diseases and conditions which are manifested by cardiac abnormalities or cardiac dysfunction can lead to heart failure. Heart failure is a pathophysiological condition in which the heart fails to pump blood at a rate commensurate with the requirements of the metabolizing tissues of the body. When the heart begins to fail, physiological mechanisms for modulating the function of the heart are utilized to increase heart rate and contractility.

The most important of the mechanisms that are responsible for modulating cardiac function are the adrenergic pathways. In a normal heart, these pathways are largely responsible for allowing cardiac pumping performance to meet the circulatory demands of increased activity by rapidly increasing or decreasing cardiac function according to circulatory demands. The cellular actions of these pathways are mediated through a family of receptors, called adrenergic receptors. There are two β-adrenergic receptor subtypes, $\beta_1$ and $\beta_2$, which, when stimulated, initiate a G-protein coupled signaling cascade, resulting in immediate stimulation of pump performance.

When the heart begins to fail, adrenergic activity is stimulated by increased sympathetic nerve activity, presynaptic facilitation of norepinephrine release and eventually, decreased neuronal norepinephrine reuptake. Increased circulating epinephrine also stimulates cardiac β-adrenergic receptors, particularly in the initial phase of heart failure.

In heart failure, the immediate stimulation of pump performance by β-adrenergic mechanisms is subsequently aided by two additional means of stabilizing or increasing cardiac function. These are an increase in plasma volume, which in turn increases preload, and hypertrophy of the cardiac myocytes, which results in more contractile elements. The subcellular mechanisms mediating these additional cardiac functions include both the β-adrenergic receptor pathways and the $\alpha_1$-adrenergic receptor pathway, among other myocellular pathways.

In the failing ventricular myocardium, the exposure to elevated levels of cognate agonists causes the adrenergic receptors to undergo regulatory changes. In particular, the $\beta_1$-adrenergic receptor exhibits down-regulation or loss of receptor protein and may also be partially uncoupled from the signaling response. $\beta_2$-adrenergic receptors are not down-regulated, but are weakly uncoupled from the signaling response. The $\alpha_1$-adrenergic receptors are slightly up-regulated and are partially uncoupled from the signaling response. These changes in adrenergic receptor expression and signaling partially withdraw the cardiac myocyte from chronic stimulation, although some adrenergic function remains. The increased agonist exposure, however, continues to chronically stimulate the remaining adrenergic signaling function, resulting in the compromise of the modulatory effects of the adrenergic system. Therefore, the prime functional capabilities of the adrenergic system, to rapidly and substantially increase or decrease cardiac function according to demand, are compromised, while the adverse effects of chronic stimulation of cardiac function remain.

Numerous compounds have been identified and used to inhibit the functions of the β-adrenergic receptors, and thus, eliminate the adverse effects of chronic myocardial stimulation through the adrenergic pathways. These compounds, often called β-adrenergic antagonists or β-blockers, interact with the β-adrenergic receptors and thereby inhibit or prevent cellular signaling by the endogenous agonists. One β-adrenergic antagonist can differ from another in a variety of ways, including by receptor subtype specificity, effect on expression of the adrenergic receptor, and effect on adrenergic receptor signaling.

Although β-adrenergic antagonists are important therapeutic tools for use in patients experiencing heart failure, these drugs are often not well tolerated by patients, causing adverse side effects, such as bradycardia, myocardial depression, dyspnea and fluid retention. The characteristics which contribute to the poor tolerability (i.e., undesirable side effects) of β-adrenergic antagonists are controversial and not well understood. See Kelly and Smith, in *Heart Disease: A Textbook Of Cardiovascular Medicine*, Chapter 16 at page 488 (5th ed., Braunwald ed., 1997).

Therefore, there is a need to develop a standardized method for screening adrenergic receptor antagonists for use in the treatment of heart failure which identifies adrenergic receptor antagonists that have good tolerability in patients.

SUMMARY OF THE INVENTION

The invention satisfies this need by providing a method of identifying adrenergic receptor antagonists having good tolerability. It has been found that adrenergic receptor antagonists having good tolerability exhibit less than about 50% inverse agonist activity and, preferably, also exhibit less than about 30% intrinsic sympathomimetic activity. Thus, the method of the invention comprises measuring the inverse agonist activity of an adrenergic receptor antagonist and, preferably, further comprises measuring the intrinsic sympathomimetic activity of the adrenergic receptor antagonist, to identify adrenergic receptor antagonists having the desired levels of activity.

For instance, one embodiment of the present invention is a method to identify a $\beta_1$ adrenergic receptor antagonist having good tolerability, which includes the steps of: (a) identifying an adrenergic receptor antagonist which binds to a $\beta_1$ adrenergic receptor; (b) measuring the basal adrenergic receptor signaling activity of the $\beta_1$ adrenergic receptor; (c) contacting the $\beta_1$ adrenergic receptor and the adrenergic receptor antagonist; (d) measuring the inverse agonist activity of the adrenergic receptor antagonist on the $\beta_1$ adrenergic receptor; and (e) identifying adrenergic receptor antagonists having less than about 50% inverse agonist activity. The method preferably further includes the steps of (f) measuring the intrinsic sympathomimetic activity of the adrenergic receptor antagonist; and (g) identifying adrenergic receptor antagonists having less than about 30% intrinsic sympathomimetic activity.

Another embodiment of the present invention is a method to identify an adrenergic receptor antagonist having good tolerability which includes the steps of: (a) measuring the basal adrenergic receptor signaling activity of an adrenergic receptor; (b) measuring the inverse agonist activity of an adrenergic receptor antagonist on the adrenergic receptor; (c) identifying adrenergic receptor antagonists having less than about 50% inverse agonist activity; (d) measuring the intrinsic sympathomimetic activity of the adrenergic receptor antagonist; and (e) identifying adrenergic receptor antagonists having less than about 30% intrinsic sympathomimetic activity.

Yet another embodiment of the present invention is a method to identify an adrenergic receptor antagonist having good tolerability, which includes the steps of (a) identifying an adrenergic receptor antagonist which binds to an adrenergic receptor expressed by a recombinant cell; (b) measuring the basal adrenergic receptor signaling activity of the adrenergic receptor; (c) measuring the inverse agonist activity of said adrenergic receptor antagonist on the adrenergic receptor; (d) measuring the intrinsic sympathomimetic activity of said adrenergic receptor antagonist on the adrenergic receptor; and (e) identifying adrenergic receptor antagonists having less than about 50% inverse agonist activity and less than about 30% intrinsic sympathomimetic activity.

A further embodiment of the present invention is a method to identify adrenergic receptor antagonists having good tolerability, which includes the steps of; (a) identifying a β adrenergic receptor antagonist which binds to a β adrenergic receptor expressed by a recombinant cell; (b) administering an effective amount of the β adrenergic receptor antagonist to a transgenic animal, wherein the myocardial cells in the heart of said transgenic animal overexpress a β adrenergic receptor which is encoded by a transgene; (c) measuring the inverse agonist activity of the β adrenergic receptor antagonist on the β adrenergic receptor; (d) measuring the intrinsic sympathomimetic activity of the β adrenergic receptor antagonist on the β adrenergic receptor; and (e) identifying β adrenergic receptor antagonists having less than about 50% inverse agonist activity and less than about 30% intrinsic sympathomimetic activity.

The invention also provides an adrenergic receptor antagonist having good tolerability. This adrenergic receptor antagonist has an inverse agonist activity of less than about 50% and an intrinsic sympathomimetic activity of less than about 10%.

Finally, the invention provides a method of treating heart failure. The method comprises identifying the need for stabilization of heart function in a patient with heart failure and administering to the patient an effective amount of an adrenergic receptor antagonist which has less than about 50% inverse agonist activity and less than about 10% intrinsic sympathomimetic activity.

BRIEF DESCRIPTION OF THE DRAWINGS

In FIG. 1B, the bars are, from left to right, metoprolol, propranolol, carvedilol, bucindolol, and xamoterol. *$P \leq 0.05$ versus metoprolol.

DETAILED DESCRIPTION OF PRESENTLY PREFERRED EMBODIMENTS OF THE INVENTION

Figure 1A:
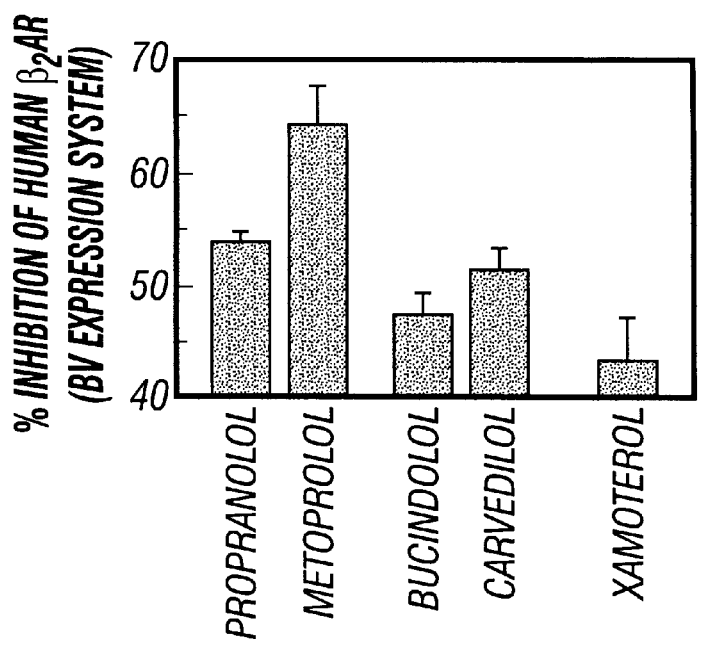
FIG. 1A is a bar graph showing the inverse agonist activity, as maximal reduction, of four β adrenergic receptor antagonists and one partial agonist in a baculovirus expression system.

As used herein, an "adrenergic receptor antagonist" is a compound which blocks, at least partially, an effect of the endogenous adrenergic receptor agonists (e.g., epinephrine and norepinephrine). Adrenergic receptor antagonists that are particularly useful in treating heart failure bind to one or more type of beta (β) adrenergic receptor and are therefore generally referred to as β blockers, β antagonists or β adrenergic antagonists. Many β adrenergic antagonists can also bind to and have a regulatory effect on alpha (α) adrenergic receptors. Therefore, as used herein, adrenergic receptor antagonists include adrenergic receptor antagonists that can bind to β and/or α adrenergic receptors.

The two β adrenergic receptor subtypes, $β_1$ and $β_2$, are coupled by the stimulatory guanine nucleotide-binding protein ($G_s$) to the effector enzyme, adenylyl cyclase, on the cell surface membrane of myocardial cells. When an agonist binds to the $β_1$ or $β_2$ receptor, the a subunit of $G_s$ ($αG_s$) increases its binding affinity for guanosine triphosphate (GTP), which then preferentially binds GTP over guanosine diphosphate (GDP). The $αG_s$-GTP complex is a powerful stimulus for the activation af adenylyl cyclase, which generates cyclic adenosine monophosphate (cAMP) from adenosine triphosphate (ATP). Cyclic AMP typically exerts its effect in a cell by activating cyclic AMP-dependent protein kinase A (PKA), which in turn phosphorylates various target proteins, thereby regulating the activity of the target proteins. Cyclic AMP exerts positive inotropic and chronotropic activity by increasing the flux of calcium through sarcolemmal slow $Ca^{2+}$ channels and increasing $Ca^{2+}$ uptake and release by the cytoplasmic reticulum. In addition, $β_1$-adrenergic receptors are coupled through $G_s$ to slow $Ca^{2+}$ channel influx by cyclic AMP-independent pathways. Activation of these pathways leads to an increase in myosin ATPase activity, resulting in increased heart pump performance.

Alpha adrenergic receptors are linked to the $G_q$ protein, which is involved in linking these receptors to phospholipase C. Signal transduction through phospholipase C may regulate activation of potassium channels and preconditioning. Preconditioning refers the situation, where the myocardium, after an ischemic insult, is protected against further ischemic insult, possibly by inhibition of adenylyl cyclase.

Unoccupied adrenergic receptors appear to possess a low level of intrinsic activity. In other words, a small percentage of the total adrenergic receptors on a cell exist, at a given time, in an active conformation that is in equilibrium with a more abundant, inactive conformation. Receptors in an active conformation initiate signal transduction even in the absence of agonists. Also, agonists bind to the active conformation of the receptor, stabilizing it and shifting the equilibrium toward the active signaling conformation.

Adrenergic receptor antagonists exert their effect through a variety of mechanisms. Some adrenergic receptor antagonists act as neutral antagonists. Neutral antagonists bind equally to the active and inactive conformations of a receptor. Neutral antagonists, therefore, have no effect on the intrinsic activity of an adrenergic receptor.

Another class of adrenergic receptor antagonists are negative antagonists, also called inverse agonists. Inverse agonists inhibit the intrinsic activity of the adrenergic receptor, presumably by binding preferentially to the inactive conformation, shifting the equilibrium toward the receptor conformation that does not initiate signaling.

Other adrenergic receptor antagonists exhibit a characteristic known as intrinsic sympathomimetic activity. Antagonists having intrinsic sympathomimetic activity are partial or weak agonists. They shift the adrenergic receptor moderately toward an active conformation, but their binding blocks the action of the more potent endogenous agonists.

Many adrenergic receptor antagonists are known (see, e.g., *Heart Disease: A Textbook Of Cardiovascular Medicine,* pages 486–488, 610–613 and 853 (5th ed., Braunwald ed., 1997)), and their tolerability can be evaluated using the method of the invention. Additional adrenergic receptor antagonists can be identified by a variety of methods well known in the art. For instance, to determine if a compound is a $\beta$ adrenergic receptor antagonist, competitive binding experiments with $^{125}$I-iodocyanopindolol (ICYP), a compound which binds selectively to $\beta$ adrenergic receptors, can be employed. Suitable conditions are described in Bristow et al., *Circulation,* 84, 1024–1039 (1991); Chidiac et al., *Molec. Pharmacol.,* 45, 490–99 (1994). Binding to $\beta_1$ or $\beta_2$ adrenergic receptors can be differentiated in a number of ways, such as competitive binding experiments using known $\beta_1$- or $\beta_2$-specific ligands or, preferably, using recombinant cells transformed to express only $\beta_1$ or $\beta_2$ adrenergic receptors (see, e.g., Tate et al., *Eur. J. Biochem.,* 196, 357–361 (1991); Samama et al., *Molec. Pharmacol.,* 45, 390–94 (1994); Chidiac et al., *Molec. Pharmacol.,* 45, 490–99 (1994); Yoshikawa et al., *Eur. Heart J.,* 17 (Supp. B), 8–16 (1996)). Binding to $\alpha_1$ adrenergic receptors may be assessed by competitive binding experiments with $^{125}$I-IBE as described in Bristow et al., *J. Cardiovasc. Phamacol.,* 19 (Suppl 1), S68–80 (1992). Compounds binding to adrenergic receptors should be confirmed to be antagonists by a functional assay, such as adenylyl cyclase activity (see below).

The present invention relates to the unexpected discovery that adrenergic receptor antagonists with low inverse agonist activity and, preferably, also no or low intrinsic sympathomimetic activity have good tolerability for use in patients suffering from heart failure. As used herein, an adrenergic receptor antagonist having good tolerability has less than about 50% inverse agonist activity, preferably less than about 40% inverse agonist activity, and even more preferably less than about 30% inverse agonist activity. An adrenergic receptor antagonist having good tolerability also preferably has less than about 30% intrinsic sympathomimetic activity, more preferably less than about 20% intrinsic sympathomimetic activity, and even more preferably less than about 10% intrinsic sympathomimetic activity.

According to the present invention, an adrenergic receptor antagonist having "good tolerability" produces limited adverse side effects in a patient to whom the adrenergic receptor antagonist is administered (i.e., the adrenergic receptor antagonist is well tolerated by the patient). Therefore, an adrenergic receptor antagonist having less than about 50% inverse agonist activity exhibits decreased adverse side effects compared to an adrenergic receptor antagonist having greater than 50% inverse agonist activity. An adrenergic receptor antagonist further having less than about 30% intrinsic sympathomimetic activity exhibits decreased adverse side effects compared to an adrenergic receptor antagonist having greater than 30% intrinsic sympathomimetic activity. The less the inverse agonist activity and the less the intrinsic sympathomimetic activity, the greater the decrease in adverse side effects.

Adverse side effects are undesirable effects or conditions which are directly or indirectly caused by the pharmacological activity of an adrenergic receptor antagonist. These adverse side effects can include bradycardia, myocardial depression, dypsnea, hypotension, congestive heart failure, worsening of asthma, worsening of chronic obstructive pulmonary disease, intermittent claudication, Raynaud's phenomenon, mental depression, increased risk of hypoglycemia (among insulin-dependent diabetic patients), easy fatigability, disturbingly vivid dreams, insomnia, impaired sexual function, or fluid retention. A decrease in such adverse side effects can refer to a decrease in the number of different side effects experienced by a patient, to a decrease in the severity of a particular side effect experienced by a patient, and/or to a decrease in the occurrence of a particular side effect experienced by a patient.

One step in the method to identify an adrenergic receptor antagonist having good tolerability includes measuring the basal adrenergic receptor signaling activity. According to the present invention, the basal activity of an adrenergic receptor is the level of measurable intrinsic signaling activity of unoccupied adrenergic receptors (i.e., receptors which are not bound by a ligand) as compared to zero receptor activity. Alternatively, the basal activity of an adrenergic receptor can be any defined level of receptor signaling activity, such as the level of activity which is achieved upon stimulation of a particular receptor (e.g., a $\beta_1$ adrenergic receptor) with a specific amount of a known agonist.

As used herein, the phrases "receptor signaling activity," "receptor activity" and "signaling activity" refer to the ability of a receptor to transduce a signal. The signal is transmitted through the signal transduction pathway, ultimately resulting in a cellular response. The magnitude of the cellular response can be measured to quantitate the receptor signaling activity. As noted above, adrenergic receptors appear to have intrinsic signaling activity. Signaling activity may also be modulated as a result of the binding of a ligand to the receptor.

Adrenergic receptor signaling activity can be quantitated by measuring any cellular response initiated by adrenergic receptor signal transduction. For instance, the adenylyl cyclase activity associated with the adrenergic receptor, the heart contractility support provided by the adrenergic receptor, the level of phosphorylation of protein kinase A associated with the adrenergic receptor, or muscle bath activity can be measured.

Adenylyl cyclase activity of an adrenergic receptor can be measured by any assay for adenylyl cyclase activity. Such assays are known in the art. For example, the generation of radiolabeled cAMP can be quantitated as a measure of adenylyl cyclase activity. See, e.g., Samama et al., *Molec. Pharmacol.,* 45, 390–94 (1994); Chidiac et al., *Molec. Pharmacol.,* 45, 490–99 (1994); T Samama et al., *J. Biol. Chem.,* 268, 4625–4636 (1993); ate et al., *Eur. J. Biochem.,* 196, 357–361 (1991).

Heart contractility support which is provided by an adrenergic receptor can be measured, for example, by measuring the myosin ATPase activity in a myocyte. Such assays are also known in the art.

Measurement of the phosphorylation of protein kinase A (or of proteins phosphorylated by protein kinase A) can be measured by any phosphorylation assay. Such assays are also known in the art. See, e.g., *Methods In Enzymology,* volume 200, "Protein Phosphorylation, Part A," (Hunter and Lefton eds., 1991). For instance, immunoassays utilizing antibodies specific for phosphotyrosines, phosphoserines and/or phosphothreonines can be used to make these measurements.

Muscle bath activity can be measured as described in Port et al., *Circulation,* 81, 929–938 (1990).

Another step in a method to identify adrenergic receptor antagonists having good tolerability includes measuring the inverse agonist activity of an adrenergic receptor antagonist on an adrenergic receptor and identifying adrenergic receptor antagonists having less than about 50% inverse agonist activity compared to basal receptor signaling activity. This step preferably further includes identifying adrenergic receptor antagonists having less than about 40% inverse antagonist activity, and even more preferably includes identifying adrenergic receptor antagonists having less than about 30% inverse antagonist activity. As noted above, inverse agonists inhibit the activity of adrenergic receptors, presumably by binding preferentially to the inactive conformation, shifting the equilibrium toward the receptor conformation that does not initiate signaling.

Any method of measuring inverse agonist activity can be used. Such methods are well known. See, e.g, Kenakin, *Pharmacol. Rev.*, 48, 413 (1996). Suitable methods include, but are not limited to, any of the methods for measuring basal adrenergic receptor activity described above, wherein the basal adrenergic receptor activity serves as a point of reference for evaluating the effect of the adrenergic receptor antagonist on the adrenergic receptor activity. Thus, an adrenergic receptor antagonist having inverse agonist activity can be identified, for example, by its ability to decrease adenylyl cyclase activity compared to basal adenylyl cyclase activity, to inhibit heart contractility support by the adrenergic receptor compared to the basal level of heart contractility support, and/or to decrease the level of phosphorylation of protein kinase A associated with the adrenergic receptor compared to the basal level of phosphorylation of protein kinase A. An adrenergic receptor antagonist having less than about 50% inverse agonist activity will produce no more than about a 50% reduction in basal adrenergic receptor activity. For instance, an adrenergic receptor antagonist having less than about 50% inverse agonist activity will inhibit basal adenylyl cyclase activity no more than about 50%. Similarly, an adrenergic receptor antagonist having less than about 40% inverse agonist activity will inhibit basal adenylyl cyclase activity no more than about 40%, and an adrenergic receptor antagonist having less than about 30% inverse agonist activity will inhibit basal adenylyl cyclase activity no more than about 30%.

An adrenergic receptor antagonist having good tolerability has less than about 50% inverse agonist activity and, preferably, also less than about 30% intrinsic sympathomimetic activity. Thus, another step in a preferred method to identify adrenergic receptor antagonists with good tolerability is to measure the intrinsic sympathomimetic activity of an adrenergic receptor antagonist. This step further includes identifying adrenergic receptor antagonists having less than about 30% intrinsic sympathomimetic activity, preferably less than about 20% intrinsic sympathomimetic activity, even more preferably less than about 10% intrinsic sympathomimetic activity. As discussed above, adrenergic receptor antagonists having intrinsic sympathomimetic activity exhibit weak agonist activity, since they shift the adrenergic receptor moderately toward an active conformation.

Any method of measuring intrinsic sympathomimetic activity can be used. Such methods are well known. See, e.g., Jasper and Insel, *Biochem. Pharmacol.*, 43, 119–130 (1992). Suitable methods include, but are not limited to, the methods described above for measurement of basal adrenergic receptor signaling activity and for measurement of inverse agonist activity. Thus, an adrenergic receptor antagonist having intrinsic sympathomimetic activity can be identified, for example, by its ability to increase adenylyl cyclase activity compared to basal adenylyl cyclase activity, to increase heart contractility support provided by the adrenergic receptor compared to the basal level of heart contractility support, and/or to increase the level of phosphorylation of protein kinase A associated with the adrenergic receptor compared to the basal level of phosphorylation of protein kinase A. For instance, an adrenergic receptor antagonist having good tolerability will have less than about a 30% increase, preferably less than about a 20% increase, even more preferably less than about a 10% increase, in adenylyl cyclase activity compared to basal adenylyl cyclase activity.

As can be seen from the above discussion, the basal adrenergic receptor signaling activity, the inverse agonist activity and the intrinsic sympathomimetic activity can all conveniently be measured in a single assay. For instance, adenylyl cyclase activity could be measured. An adrenergic receptor antagonist having good tolerability would produce no more than about a 50% reduction, and less than about a 30% increase, in adenylyl cyclase activity compared to basal adenylyl cyclase activity.

The assays of receptor signaling activity can be performed in a variety of in vitro systems, as is known in the art. For instance, the assays can be performed using whole hearts, tissues (e.g., left ventricle myocardium), cells (e.g., myocytes) and cell membranes (e.g., myocyte membranes). Preferably, however, recombinant cells expressing one or more adrenergic receptor are used.

A recombinant cell which expresses an adrenergic receptor is preferably produced by transforming a host cell with one or more recombinant molecules, each comprising one or more nucleic acid molecules encoding an adrenergic receptor operatively linked to an expression vector containing one or more transcription control sequences. The phrase, "operatively linked" refers to insertion of a nucleic acid molecule into an expression vector in a manner such that the molecule is able to be expressed when transformed into a host cell. As used herein, an expression vector is a vector that is capable of transforming a host cell and of effecting expression of a specified nucleic acid molecule. The expression vector may be capable of replicating within the host cell or may integrate into one or more chromosomes of the host cell. Expression vectors can be either prokaryotic or eukaryotic, and are typically viruses or plasmids. Expression vectors useful in the present invention include any vectors that function (i.e., direct gene expression) in recombinant cells as described herein, including in bacterial, fungal, insect and mammalian cells. Preferred expression vectors can direct gene expression in insect and mammalian cells, more preferably in mammalian cells.

Nucleic acid molecules encoding adrenergic receptors can be operatively linked to expression vectors containing regulatory sequences such as transcription control sequences, translation control sequences, origins of replication, and other regulatory sequences that are compatible with the recombinant cell and that control the expression of nucleic acid molecules encoding adrenergic receptors. In particular, recombinant molecules encoding adrenergic receptors include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in the host cell. A variety of such transcription control sequences are known to those skilled in the art. Preferred transcription control sequences include those which function in bacterial, yeast, insect and mammalian cells. Transcription control sequences useful in a recombinant cell as described herein can also include naturally occurring transcription control sequences which are naturally associated with an adrenergic receptor prior to isolation.

According to the present invention, a recombinant molecule is a molecule which includes at least one of any nucleic acid molecule encoding an adrenergic receptor operatively linked to at least one of any transcription control sequence capable of effectively regulating expression of the nucleic acid molecule(s) in the cell to be transformed.

Preferred recombinant molecules include nucleic acid molecules encoding a $\beta_1$ adrenergic receptor, a $\beta_2$ adrenergic receptor, or an $\alpha_1$ adrenergic receptor. Particularly preferred recombinant molecules include nucleic acid molecules encoding a $\beta_1$ adrenergic receptor. Nucleic acid molecules encoding adrenergic receptors are known in the art. See, e.g., Frielle et al., *Proc. Nat'l. Acad. Sci. USA*, 84, 7920–7924 (1987); Tate et al., *Eur. J. Biochem.*, 196, 357–361 (1991); Samama et al., *J. Biol. Chem.*, 268, 4625–4636 (1993); Samama et al., *Molec. Pharmacol.*, 45, 390–94 (1994); Chidiac et al., *Molec. Pharmacol.*, 45, 490–99 (1994); Yoshikawa et al., *Eur. Heart J.*, 17 (Supp. B), 8–16 (1996); Kenakin, *Pharmacol. Rev.*, 48, 413 (1996).

A recombinant cell of the present invention includes any cell transformed with at least a nucleic acid molecule encoding an adrenergic receptor. In another embodiment, a recombinant cell of the present invention includes a cell transformed with nucleic acid molecules encoding an adrenergic receptor, a $G_s$ protein and adenylyl cyclase. See, Kenakin, *Pharmacol. Rev.*, 48, 413 (1996). Particularly preferred recombinant cells are derived from AF8, Sf9, CHW, COS-7, or CHO host cells. See, e.g., Tate et al., *Eur. J. Biochem.*, 196, 357–361 (1991); Samama et al., *J. Biol. Chem.*, 268, 4625–4636 (1993); Samama et al., *Molec. Pharmacol.*, 45, 390–94 (1994); Chidiac et al., *Molec. Pharmacol.*, 45, 490–99 (1994); Yoshikawa et al., *Eur. Heart J.*, 17 (Supp. B), 8–16 (1996).

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

In accordance with the present invention, recombinant cells can be used to produce adrenergic receptors by culturing such cells under conditions effective to produce such a protein. Effective conditions to produce a protein include, but are not limited to, appropriate media, bioreactor, temperature, pH and oxygen conditions that permit protein production. An appropriate medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

An adrenergic receptor protein expressed by a recombinant cell is preferably retained on the outer surface of the recombinant cell membrane. In a preferred embodiment, a recombinant cell useful in a method of the present invention expresses at least about 0.5 pmol, and more preferably, at least about 1.0 pmol, and even more preferably, at least about 2.0 pmol of adrenergic receptor per milligram of protein on the surface of the recombinant cell. Methods of measuring the amounts of adrenergic receptors and proteins expressed on the surfaces of recombinant cells are known in the art. See, e.g., Bristow et al., *Molec. Pharmacol.*, 35, 295–303 (1989).

Yet another embodiment of the present invention relates to a method to identify adrenergic receptor antagonists having good tolerability which includes the steps of (a) identifying a $\beta$ adrenergic receptor antagonist which binds to a $\beta$ adrenergic receptor expressed by a recombinant cell; (b) administering an effective amount of the $\beta$ adrenergic receptor antagonist to a transgenic animal overexpressing the $\beta$ adrenergic receptor; (c) measuring the inverse agonist activity of the $\beta$ adrenergic receptor antagonist on the $\beta$ adrenergic receptor; (d) measuring the intrinsic sympathomimetic activity of the $\beta$ adrenergic receptor antagonist on the $\beta$ adrenergic receptor; and (e) identifying $\beta$ adrenergic receptor antagonists having less than about 50% inverse agonist activity and less than about 30% intrinsic sympathomimetic activity. Preferably the $\beta$ adrenergic receptor antagonist is a $\beta_1$ adrenergic receptor antagonist and the transgenic animal expresses a $\beta_1$ adrenergic receptor.

In this embodiment, a transgenic animal which overexpresses a $\beta$ adrenergic receptor serves as an in vivo system to evaluate the activity of adrenergic receptor antagonists. According to the present invention, the term, "overexpresses", refers to the expression of an adrenergic receptor transgene by the myocardial cells of a transgenic animal which results in a level of expression of adrenergic receptor protein by the myocardial cell which exceeds the level of expression of adrenergic receptor protein by myocardial cells which do not contain a transgene (i.e., myocardial cells which express only endogenous adrenergic receptor). In a preferred embodiment, the transgenic animal is a transgenic mouse, even more preferably a transgenic mouse overexpressing human $\beta_1$ adrenergic receptor.

According to the method of the present invention, an effective amount of an adrenergic receptor antagonist to administer to a transgenic animal includes an amount that is capable of binding to and causing measurable activity by an adrenergic receptor in the heart of the transgenic animal. An amount that is toxic to an animal comprises any amount that causes damage to the structure or function of an animal (i.e., poisonous).

Methods for measuring the inverse agonist activity of a β adrenergic receptor antagonist and of measuring the intrinsic sympathomimetic activity of a β adrenergic receptor antagonist have been previously described herein and are generally applicable to the above method using hearts, tissues or cells isolated from the transgenic animals. See, e. g., Bond et al., *Nature*, 374, 272–276 (1995); Sponer et al., *J. Cardiovascular Pharmacol.*, 9, 317–327 (1987). Similarly, adrenergic receptor antagonists having less than about 50% inverse agonist activity and less than about 30% intrinsic sympathomimetic activity identified by the above method can have the characteristics described above.

Measurable activity by an adrenergic receptor in the heart of the transgenic animal can, alternatively, be assessed as a change in heart function of the transgenic animal compared to untreated animals. See, e.g., Bond et al., *Nature*, 374, 272–276 (1995); Sponer et al., *J. Cardiovascular Pharmacol.*, 9, 317–327 (1987). For example, the rate of contraction of the heart, the peak force of the heart, and/or the rate of relaxation of the heart can be measured as an indicator of the adrenergic receptor antagonist activity in the heart of a transgenic animal as described herein. Thus, for an adrenergic receptor antagonist having good tolerability, the rate of contraction of the heart should be reduced by no more than 50% and increased by no more than 30% in transgenic animals receiving the adrenergic receptor antagonist as compared to untreated animals. Methods of making such measurements are well known in the art.

Also, the use of trangenic animals allows the direct assessment of many adverse side effects. See above for a discussion of adverse side effects of adrenergic receptor antagonists.

According to the present invention, a transgenic mouse is a mouse which includes a recombinant nucleic acid molecule (i.e., transgene) that has been introduced into the genome of the mouse at the embryonic stage of the mouse's development. As such, the transgene will be present in all of the germ cells and somatic cells of the mouse. Methods for the introduction of a transgene into a mouse embryo are known in the art and are described in detail in Hogan et al., *Manipulating the Mouse Embryo. A Laboratory Manual*, Cold Spring Harbor press, Cold Spring Harbor, N.Y., 1986, which is incorporated by reference herein in its entirety. For example, a recombinant nucleic acid molecule (i.e., transgene) can be injected into the male pronucleus of a fertilized mouse egg to cause one or more copies of the recombinant nucleic acid molecule to be retained in the cells of the developing mouse. A mouse retaining the transgene, also called a "founder" mouse, usually transmits the transgene through the germ line to the next generation of mice, establishing transgenic lines. According to the present invention, a transgenic mouse also includes all progeny of a transgenic mouse that inherit the transgene.

The β adrenergic receptor transgene is constructed and cloned by standard methods known in the art. Such standard methods are disclosed, for example, in Sambrook et al., 1989, *Molecular Cloning: A Laboratory Manual*, Cold Spring Harbor Labs Press. The reference Sambrook et al., ibid., is incorporated by reference herein in its entirety.

More particularly, the β adrenergic receptor transgene is ligated into a prokaryotic cloning vector. Prokaryotic cloning vectors and methods for using such vectors to clone DNA are well known in the art. In addition to the β adrenergic receptor cDNA as described above, the transgene is constructed to include a promoter selected to drive expression of the transgene exclusively in the heart. Further, the transgene includes 5' and 3' flanking introns, and polyadenylation sequences. Preferably, the promoter is an α myosin heavy chain promoter which is operatively linked to the β adrenergic receptor cDNA. The phrase, operatively linked, refers to insertion of nucleic acid sequences, including the transcriptional promoter sequences, in a manner such that the molecule is able to be expressed in cells when integrated into a host genome. Transcription control sequences are sequences which control the initiation, elongation, and termination of transcription. Particularly important transcription control sequences are those which control transcription initiation, such as promoter and enhancer sequences. Suitable transcription control sequences include any transcription control sequence that can function in the transgene expression system of the present invention.

Transgene sequences are cloned using a standard prokaryotic cloning system, and the transgene products are excised from the prokaryotic vector, purified, and injected into the pronuclei of fertilized mouse eggs. Stable integration of the transgene into the genome of the transgenic embryos allows permanent transgenic mouse lines to be established.

Transgenic mice useful in the practice of the invention are described in Milano et al., *Science*, 264, 582–586 (1994), Milano et al., *J. Thoracic Cardiovasc. Surg.*, 109, 236–241 (1995), Bond et al., *Nature*, 374, 272–276 (1995), and the copending application entitled "Transgenic Model And Treatment For Heart Disease," filed on even date herewith, the complete disclosures of which are incorporated herein by reference. See also, Bertin et al., *Cardiovasc. Res.*, 27, 1606–1612 (1993) and PCT application WO 94/04668.

In accordance with the present invention, acceptable protocols to administer an adrenergic receptor antagonist include the mode of administration and the effective amount of adrenergic receptor antagonist administered to an animal, including individual dose size, number of doses and frequency of dose administration. Determination of such protocols can be accomplished by those skilled in the art. Suitable modes of administration can include, but are not limited to, oral, nasal, topical, transdermal, rectal, and parenteral routes. Preferred parenteral routes can include, but are not limited to, subcutaneous, intradermal, intravenous, intramuscular and intraperitoneal routes. Preferred topical routes include inhalation by aerosol (i.e., spraying) or topical surface administration to the skin of an animal. The preferred route of administration is oral.

Yet another embodiment of the present invention relates to an adrenergic receptor antagonist having good tolerability. Such an adrenergic receptor antagonist is characterized by having less than about 50% inverse agonist activity and less than about 10% intrinsic sympathomimetic activity. Preferably the adrenergic receptor antagonist has less than about 40% inverse agonist activity, even more preferably less than about 30% inverse agonist activity.

Another embodiment of the present invention relates to a method to treat heart failure. Such a method includes the steps of identifying the need for stabilization of heart function in a patient with heart failure, and administering to the patient an effective amount of an adrenergic receptor antagonist which has less than about 50% inverse agonist activity and less than about 10% intrinsic sympathomimetic activity with respect to the adrenergic receptor. Preferably the adrenergic receptor antagonist has less than about 40% inverse agonist activity, even more preferably less than about 30% inverse agonist activity.

The need for stabilization of heart function in a patient with heart failure can be identified by a variety of methods well known in the art. In particular, patients in need of stabilization of heart function are those who exhibit the normal signs and symptoms of heart failure. See, e.g., *Heart Disease: A Textbook Of Cardiovascular Medicine,* (5th ed., Braunwald ed., 1997).

An effective administration protocol (i.e., administering an adrenergic receptor antagonist in an effective manner) comprises suitable dose parameters and modes of administration that result in stabilization of heart function in a patient with heart failure. Effective dosage forms, modes of administration and dosage amounts, may be determined empirically, and making such determinations is within the skill of the art. It is understood by those skilled in the art that the dosage amount will vary with the activity of the particular agent employed, the severity of the heart failure, the route of administration, the rate of excretion, the duration of the treatment, the identity of any other drugs being administered to the patient, the age and size of the patient, and like factors well known in the medical art.

In general, a suitable daily dose of an adrenergic receptor antagonist will be that amount of the agent which is the lowest dose effective to produce a therapeutic effect. A suggested daily dosage of an adrenergic receptor antagonist for treatment of heart failure is about 1–1000 mg/day. However, the total daily dosage of the agent will be determined by an attending physician within the scope of sound medical judgment. If desired, the effective daily dose may be administered as two, three, four, five, six or more sub-doses, administered separately at appropriate intervals throughout the day. Thus, it is within the scope of the present invention that a suitable number of doses, as well as the time periods between administration, includes any number required to cause stabilization of heart function.

Suitable modes of administration can include, but are not limited to, oral, nasal, topical, transdermal, rectal, and parenteral routes. Preferred parenteral routes include, but are not limited to, subcutaneous, intradermal, intravenous, intramuscular and intraperitoneal routes. Preferred is oral administration.

While it is possible for an adrenergic receptor antagonist to be administered alone, it is preferable to administer the compound as a pharmaceutical formulation (composition). The pharmaceutical compositions comprise one or more adrenergic receptor antagonists as an active ingredient in admixture with one or more pharmaceutically-acceptable carriers and, optionally, with one or more other compounds, drugs or other materials. A pharmaceutically acceptable carrier refers to any substance suitable as a vehicle for delivering an adrenergic receptor antagonist of the present invention to a suitable in vivo site of action. Preferred carriers are capable of maintaining adrenergic receptor antagonists of the present invention in a form that is capable of binding to and regulating the activity of an adrenergic receptor. Each carrier must be "acceptable" in the sense of being compatible with the other ingredients of the formulation and not injurious to the patient. Suitable carriers are well known in the art and include those carriers currently being used in pharmaceutical formulations of adrenergic receptor antagonists.

Pharmaceutical formulations of the present invention include those suitable for oral, nasal, topical, transdermal, rectal, and/or parenteral administration. Regardless of the route of administration selected, the adrenergic receptor antagonists are formulated into pharmaceutically-acceptable dosage forms by conventional methods known to those of skill in the art.

The amount of active ingredient that will be combined with a carrier material to produce a single dosage form will vary depending upon the host being treated, the particular mode of administration and all of the other factors described above. The amount of active ingredient which will be combined with a carrier material to produce a single dosage form will generally be that amount of the agent which is the lowest dose effective to produce a therapeutic effect.

Methods of preparing pharmaceutical formulations or compositions include the step of bringing into association an adrenergic receptor antagonist with the carrier and, optionally, one or more accessory ingredients. In general, the formulations are prepared by uniformly and intimately bringing into association an adrenergic receptor antagonist with liquid carriers, or finely divided solid carriers, or both, and then, if necessary, shaping the product. Suitable and necessary accessory ingredients are well known in the art.

The following experimental results are provided for purposes of illustration and are not intended to limit the scope of the invention.

EXAMPLES

Example 1

Measuring Inverse Agonist Activity

This example describes the measurement of the inverse agonist activity of several known adrenergic receptor antagonists. The adrenergic receptor antagonists tested were carvedilol, bucindolol, metoprolol and propranolol. Xamoterol, a partial agonist, was also tested.

Carvedilol is a high affinity blocking agent for $\beta_1$, $\beta_2$ and $\beta_1$ adrenergic receptors with a descending rank order of potency of $\beta_1 > \alpha_1 >> \beta_2$. See Yoshikawa, et al., *Eur. Heart J.,* 17 (Suppl B), 8–16 (1996). Bucindolol and propranolol are nonselective for $\beta_1$ and $\beta_2$ adrenergic receptors, i.e., they bind equally to both receptors. Id. Metoprolol and xamoterol are highly selective for $\beta_1$ adrenergic receptors. Id.

Sf9 cells were transfected with a baculovirus expression system coding for human $\beta_1$ or $\beta_2$ receptors as described in Chidiac et al., *Molec. Pharmacol.,* 45, 490–499 (1994). Sf9 cells expose $\beta_1$ or $\beta_2$ receptors at ultra-high density (~10 pmol~mg$^{-1}$).

Adenylyl cyclase activity of Sf9 membranes was measured as described in Chidiac et al., *Molec. Pharmacol.,* 45, 490–499 (1994). The inhibition of basal cAMP generation in this system is a measure of inverse agonism.

Figure 1B:
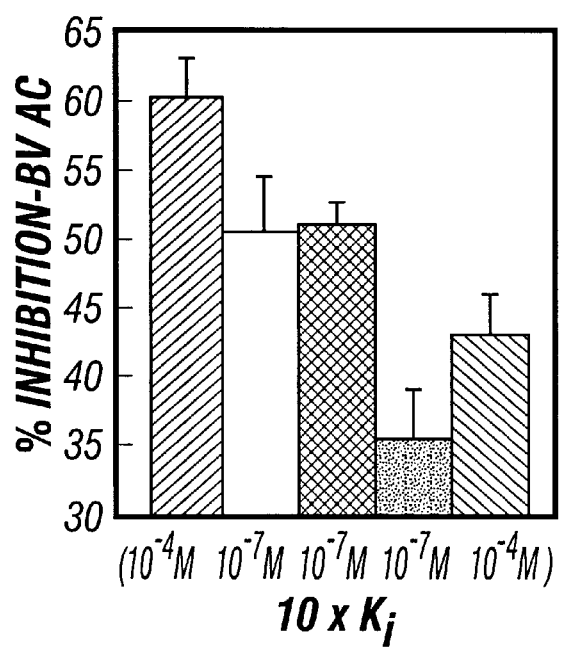
FIG. 1B is a bar graph showing the inverse agonist activity, as a degree of reduction referenced against concentrations that are approximately 10× the $K_i$ for human $β_2$ adrenergic receptors, of four β adrenergic receptor antagonists and one partial agonist in a baculovirus expression system.

The results are presented in FIGS. 1A–1B. The data are expressed as a percent reduction in basal adenylyl cyclase (AC) activity as either the maximal reduction of AC (FIG. 1A) or the degree of reduction referenced against concentrations that are approximately 10× the $K_i$ for human $\beta_2$ adrenergic receptors (AR) (FIG. 1B).

Using the maximum degree of inhibition (FIG. 1A), propranolol and metoprolol have relatively large amounts of inverse agonist activity, compared to carvedilol, bucindolol and xamoterol. The three latter compounds exhibited less than about a 50% reduction in adenylyl cyclase basal activity, and bucindolol and xamoterol exhibited less than about a 30% reduction in adenylyl cyclase basal activity. Using a concentration 10×$K_i$ for the $\beta_2$ receptor, the rank order of inverse agonist activity was metoprolol>propranolol≧carvedilol>xamoterol>bucindolol (FIG. 1B; columns in order from left to right=metoprolol, propranolol, carvedilol, bucindolol, xamoterol). All of the compounds, except metoprolol, exhibited less than about 50% inhibition.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

We claim:

1. A method to identify a $\beta_1$ adrenergic receptor antagonist having good tolerability, comprising:
   (a) identifying an adrenergic receptor antagonist which binds to a $\beta_1$ adrenergic receptor;
   (b) measuring the basal adrenergic receptor signaling activity of said $\beta_1$ adrenergic receptor;
   (c) contacting said $\beta_1$ adrenergic receptor and said adrenergic receptor antagonist;
   (d) measuring the inverse agonist activity of said adrenergic receptor antagonist on said $\beta_1$ adrenergic receptor; and
   (e) identifying adrenergic receptor antagonists having less than about 50% inverse agonist activity.

2. The method of claim 1, further comprising:
   (f) measuring the intrinsic sympathomimetic activity of the adrenergic receptor antagonist on said $\beta_1$ adrenergic receptor; and
   (g) identifying adrenergic receptor antagonists having less than about 30% intrinsic sympathomimetic activity.

3. The method of claim 1, wherein said basal adrenergic receptor signaling activity is measured by a method selected from the group consisting of determining the basal adenylyl cyclase activity of said $\beta_1$ adrenergic receptor, measuring the basal heart contractility support provided by said $\beta_1$ adrenergic receptor and measuring the basal level of phosphorylation of protein kinase A associated with said $\beta_1$ adrenergic receptor.

4. The method of claim 1, wherein said inverse agonist activity is measured by a method selected from the group consisting of determining the adenylyl cyclase activity of said $\beta_1$ adrenergic receptor, measuring the heart contractility support provided by said $\beta_1$ adrenergic receptor and measuring the level of phosphorylation of protein kinase A associated with said $\beta_1$ adrenergic receptor.

5. The method of claim 2, wherein said intrinsic sympathomimetic activity is measured by a method selected from the group consisting of determining the adenylyl cyclase activity of said $\beta_1$ adrenergic receptor, measuring the heart contractility support provided by said $\beta_1$ adrenergic receptor and measuring the level of phosphorylation of protein kinase A associated with said $\beta_1$ adrenergic receptor.

6. The method of claim 1, wherein said step (e) comprises identifying adrenergic receptor antagonists having less than about 40% inverse agonist activity.

7. The method of claim 1, wherein said step (e) comprises identifying adrenergic receptor antagonists having less than about 30% inverse agonist activity.

8. The method of claim 2, wherein said step (g) comprises identifying adrenergic receptor antagonists having less than about 20% intrinsic sympathomimetic activity.

9. The method of claim 2, wherein said step (g) comprises identifying $\beta_1$ adrenergic receptor antagonists having less than about 10% intrinsic sympathomimetic activity.

10. A method to identify an adrenergic receptor antagonist having good tolerability, comprising:
    (a) measuring the basal adrenergic receptor signaling activity of an adrenergic receptor;
    (b) measuring the inverse agonist activity of an adrenergic receptor antagonist on said adrenergic receptor;
    (c) identifying adrenergic receptor antagonists having less than about 50% inverse agonist activity;
    (d) measuring the intrinsic sympathomimetic activity of the adrenergic receptor antagonist; and
    (e) identifying adrenergic receptor antagonists having less than about 30% intrinsic sympathomimetic activity.

11. The method of claim 10, wherein said basal adrenergic receptor signaling activity is measured by a method selected from the group consisting of determining the basal adenylyl cyclase activity of said adrenergic receptor, measuring the basal heart contractility support provided by said adrenergic receptor and measuring the basal level of phosphorylation of protein kinase A associated with said adrenergic receptor.

12. The method of claim 10, wherein said inverse agonist activity is measured by a method selected from the group consisting of determining the adenylyl cyclase activity of said adrenergic receptor, measuring the heart contractility support provided by said adrenergic receptor and measuring the level of phosphorylation of protein kinase A associated with said adrenergic receptor.

13. The method of claim 10, wherein said intrinsic sympathomimetic activity is measured by a method selected from the group consisting of determining the adenylyl cyclase activity of said adrenergic receptor, measuring the heart contractility support provided by said adrenergic receptor and measuring the level of phosphorylation of protein kinase A associated with said adrenergic receptor.

14. The method of claim 10, wherein said step (c) comprises identifying compounds having less than about 40% inverse agonist activity.

15. The method of claim 10, wherein said step (c) comprises identifying compounds having less than about 30% inverse agonist activity.

16. The method of claim 10, wherein said step (e) comprises identifying compounds having less than about 20% intrinsic sympathomimetic activity.

17. The method of claim 10, wherein said step (e) comprises identifying compounds having less than about 10% intrinsic sympathomimetic activity.

18. The method of claim 10, wherein said adrenergic receptor is selected from the group consisting of a $\beta_1$ adrenergic receptor, a $\beta_2$ adrenergic receptor and an $\alpha_1$ adrenergic receptor.

19. The method of claim 10, wherein said adrenergic receptor is a $\beta_1$ adrenergic receptor.

20. A method to identify an adrenergic receptor antagonist having good tolerability, comprising:
    (a) identifying an adrenergic receptor antagonist which binds to an adrenergic receptor expressed by a recombinant cell;
    (b) measuring the basal adrenergic receptor signaling activity of said adrenergic receptor;
    (c) measuring the inverse agonist activity of said adrenergic receptor antagonist on said adrenergic receptor;
    (d) measuring the intrinsic sympathomimetic activity of said adrenergic receptor antagonist on said adrenergic receptor; and
    (e) identifying adrenergic receptor antagonists having less than about 50% inverse agonist activity and less than about 30% intrinsic sympathomimetic activity.

21. The method of claim 20, wherein said recombinant cell expresses at least about 0.5 pmol of said adrenergic receptor per milligram of protein on the surface of said recombinant cell.

22. The method of claim 20, wherein said basal adrenergic receptor signaling activity is measured by a method selected from the group consisting of determining the basal adenylyl cyclase activity of said adrenergic receptor, measuring the basal heart contractility support of said adrenergic receptor and measuring the basal level of phosphorylation of protein kinase A associated with said adrenergic receptor.

23. The method of claim 20, wherein said inverse agonist activity is measured by a method selected from the group consisting of determining the adenylyl cyclase activity of said adrenergic receptor, measuring the heart contractility support provided by said adrenergic receptor and measuring the level of phosphorylation of protein kinase A associated with said adrenergic receptor.

24. The method of claim 20, wherein said intrinsic sympathomimetic activity is measured by a method selected from the group consisting of determining the adenylyl cyclase activity of said adrenergic receptor, measuring the heart contractility support provided by said adrenergic receptor and measuring the level of phosphorylation of protein kinase A associated with said adrenergic receptor.

25. The method of claim 20, wherein said adrenergic receptor is selected from the group consisting of a $\beta_1$ adrenergic receptor, a $\beta_2$ adrenergic receptor, and an $\alpha$ adrenergic receptor.

26. The method of claim 20, wherein said adrenergic receptor is a $\beta_1$ adrenergic receptor.

27. The method of claim 20, wherein said recombinant cell is derived from a cell selected from the group consisting of AF8, Sf9, CHW and CHO.

28. A method to treat heart failure, comprising:
  (a) identifying the need for stabilization of heart function in a patient with heart failure; and
  (b) administering to said patient an effective amount of an adrenergic receptor antagonist which has less than about 50% inverse agonist activity and less than about 10% intrinsic sympathomimetic activity with respect to said adrenergic receptor.

* * * * *